(12) United States Patent
Violante et al.

(10) Patent No.: US 8,386,061 B2
(45) Date of Patent: Feb. 26, 2013

(54) METHODS FOR DESIGNING A CUSTOMIZED DENTAL PROSTHESIS USING DIGITAL IMAGES OF A PATIENT

(75) Inventors: Kimberly L. Violante, York, PA (US); Arlo King, Lumberton, NJ (US); Jon Jackson, Vancouver, WA (US)

(73) Assignee: DENTSPLY International Inc., York, PA (US)

( * ) Notice: Subject to any disclaimer, the term of this patent is extended or adjusted under 35 U.S.C. 154(b) by 313 days.

(21) Appl. No.: 12/455,443

(22) Filed: Jun. 2, 2009

(65) Prior Publication Data

US 2010/0076581 A1    Mar. 25, 2010

Related U.S. Application Data

(60) Provisional application No. 61/205,797, filed on Jan. 23, 2009, provisional application No. 61/130,622, filed on Jun. 2, 2008.

(51) Int. Cl.
*G06F 19/00* (2011.01)
*A61C 3/00* (2006.01)

(52) U.S. Cl. .......................................... 700/98; 433/24
(58) Field of Classification Search .................... 700/98; 705/2; 433/24, 199.1, 215, 223
See application file for complete search history.

(56) References Cited

U.S. PATENT DOCUMENTS

| | | | |
|---|---|---|---|
| 4,583,947 A | 4/1986 | Hazar | |
| 4,681,543 A | 7/1987 | Monroy | |
| 5,011,405 A | 4/1991 | Lemchen | |
| 5,027,281 A | 6/1991 | Rekow et al. | |
| 5,055,039 A | 10/1991 | Abbatte et al. | |
| 5,139,419 A | 8/1992 | Andreiko et al. | |
| 5,273,429 A | 12/1993 | Rekow et al. | |
| 5,395,238 A | 3/1995 | Andreiko et al. | |
| 5,452,219 A | 9/1995 | Dehoff et al. | |
| 5,691,905 A | 11/1997 | Dehoff et al. | |
| 5,718,585 A | 2/1998 | Dehoff et al. | |
| 5,798,924 A | 8/1998 | Eufinger et al. | |
| 5,851,115 A | 12/1998 | Carlson et al. | |
| 5,879,158 A | 3/1999 | Doyle et al. | |
| 5,882,192 A | 3/1999 | Bergusen | |
| 5,975,893 A | 11/1999 | Chisti et al. | |
| 6,007,332 A | 12/1999 | O'Brien | |
| 6,049,743 A | 4/2000 | Baba | |
| 6,068,482 A | 5/2000 | Snow | |
| 6,089,868 A | 7/2000 | Jordan et al. | |
| 6,152,731 A | 11/2000 | Jordan et al. | |
| 6,200,278 B1 * | 3/2001 | Arnett | 600/587 |
| 6,227,850 B1 | 5/2001 | Chisti et al. | |
| 6,244,861 B1 | 6/2001 | Andreiko et al. | |
| 6,250,918 B1 | 6/2001 | Sachdeva et al. | |

(Continued)

FOREIGN PATENT DOCUMENTS

EP    0360657 A1    3/1990
EP    0502227 B1    11/1996

(Continued)

*Primary Examiner* — Dave Robertson
(74) *Attorney, Agent, or Firm* — David A. Zdurne; Douglas J. Hura; Leana Levin

(57) ABSTRACT

Methods and systems for producing customized dental restoration and prosthesis, particularly denture prescriptions using a computer software program are provided. In this system, digital photographs of the patient to be fitted with the denture are taken, and the photographs are transferred to the software program. Based on these photographs, the program makes certain calculations. The program then prompts the dental professional to select the desired materials and structure for the denture. Based on this input, the program automatically produces a prescription for the denture. The digital prescription is sent to a dental laboratory for making the denture.

18 Claims, 12 Drawing Sheets

U.S. PATENT DOCUMENTS

| | | |
|---|---|---|
| 6,309,215 B1 | 10/2001 | Phan et al. |
| 6,318,994 B1 | 11/2001 | Chishti et al. |
| 6,358,047 B2 | 3/2002 | Lehman |
| 6,464,496 B1 | 10/2002 | Sachdeva et al. |
| 6,688,885 B1 | 2/2004 | Sachdeva et al. |
| 6,786,726 B2 | 9/2004 | Lehman et al. |
| 7,001,178 B2 | 2/2006 | Grunenfelder et al. |
| 7,029,275 B2 | 4/2006 | Rubbert et al. |
| 7,035,702 B2 | 4/2006 | Jelonek et al. |
| 7,064,830 B2 | 6/2006 | Giogianni et al. |
| 7,118,374 B2 | 10/2006 | Culp |
| 7,128,573 B2 * | 10/2006 | Pameijer et al. ............... 433/26 |
| 7,156,655 B2 * | 1/2007 | Sachdeva et al. ............... 433/24 |
| 7,215,803 B2 | 5/2007 | Marshall |
| 7,333,874 B2 | 2/2008 | Taub et al. |
| 7,474,932 B2 * | 1/2009 | Geng ............................ 700/98 |
| 7,590,462 B2 * | 9/2009 | Rubbert et al. ............... 700/98 |
| 7,711,252 B2 * | 5/2010 | Konno et al. ................. 396/16 |
| 7,717,708 B2 * | 5/2010 | Sachdeva et al. ............ 433/24 |
| 8,092,220 B2 * | 1/2012 | Wiedmann ................. 433/202.1 |
| 2002/0010568 A1 | 1/2002 | Rubbert et al. |
| 2002/0025503 A1 | 2/2002 | Chapoulaud et al. |
| 2004/0152036 A1 | 8/2004 | Abolfathi et al. |
| 2004/0248066 A1 | 12/2004 | Recigno |
| 2008/0060652 A1 * | 3/2008 | Selvarajan et al. ...... 128/206.21 |
| 2008/0195418 A1 | 8/2008 | Parker et al. |
| 2008/0270175 A1 * | 10/2008 | Rodriguez et al. ................ 705/2 |
| 2010/0323329 A1 * | 12/2010 | Adusumilli et al. .......... 433/213 |
| 2010/0332253 A1 * | 12/2010 | Adusimilli et al. ............... 705/2 |
| 2011/0045442 A1 * | 2/2011 | Adusimilli et al. ........ 433/201.1 |

FOREIGN PATENT DOCUMENTS

| | | |
|---|---|---|
| EP | 1486901 A2 | 12/2004 |
| EP | 1935369 A1 | 6/2008 |
| WO | 8603292 A1 | 6/1986 |
| WO | 9102955 A1 | 3/1991 |
| WO | 9111959 A1 | 8/1991 |
| WO | 9515731 A1 | 6/1995 |
| WO | 9703622 A1 | 2/1997 |
| WO | 9832394 A1 | 7/1998 |
| WO | 9934747 A1 | 7/1999 |
| WO | 0016045 A1 | 3/2000 |
| WO | 0026847 A1 | 5/2000 |
| WO | 0147405 A2 | 7/2001 |
| WO | 0151005 A2 | 7/2001 |
| WO | 2005008441 A2 | 1/2005 |
| WO | 2007084727 A1 | 7/2007 |
| WO | 2007103303 A2 | 9/2007 |
| WO | 2008039544 A1 | 4/2008 |

* cited by examiner

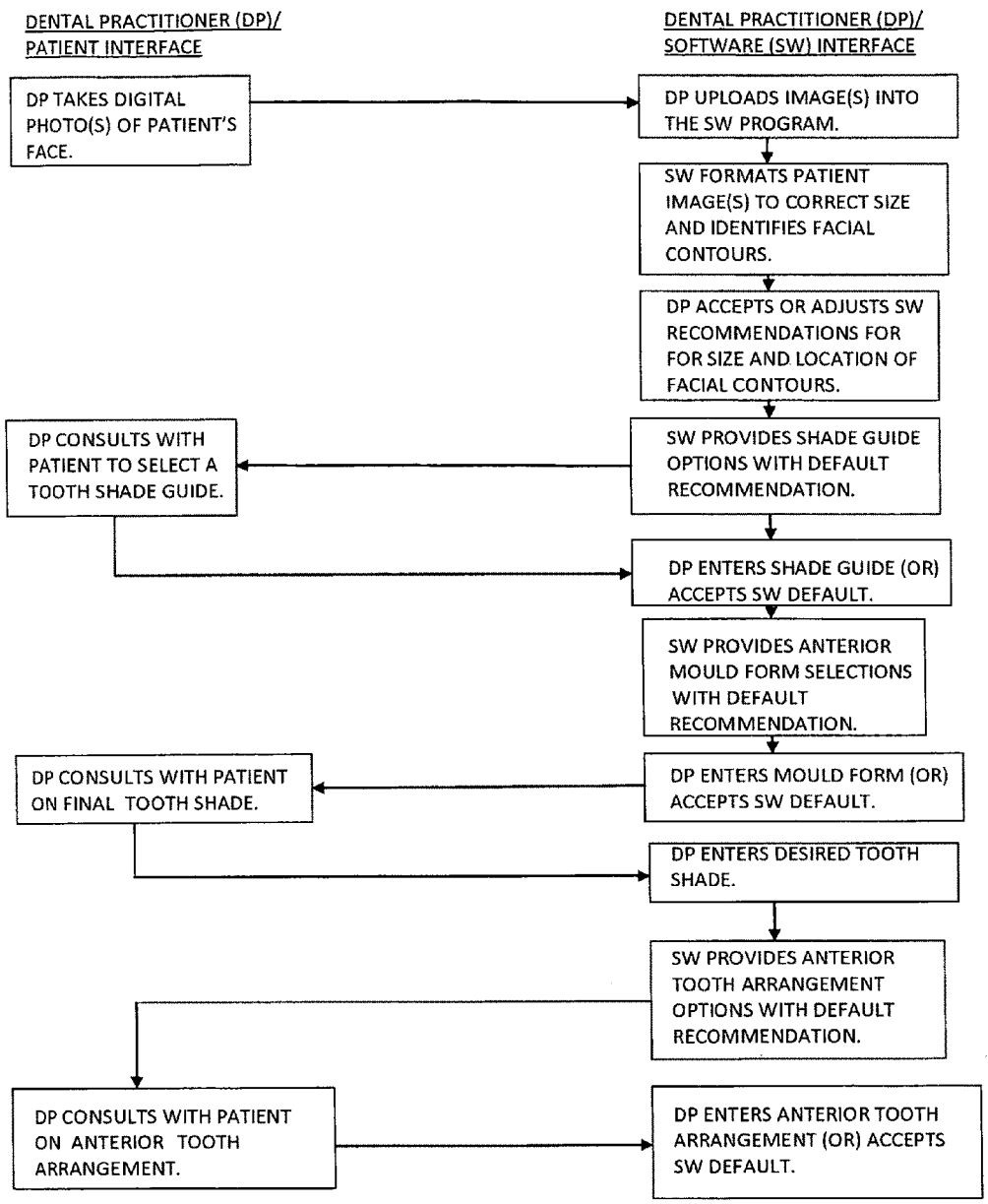

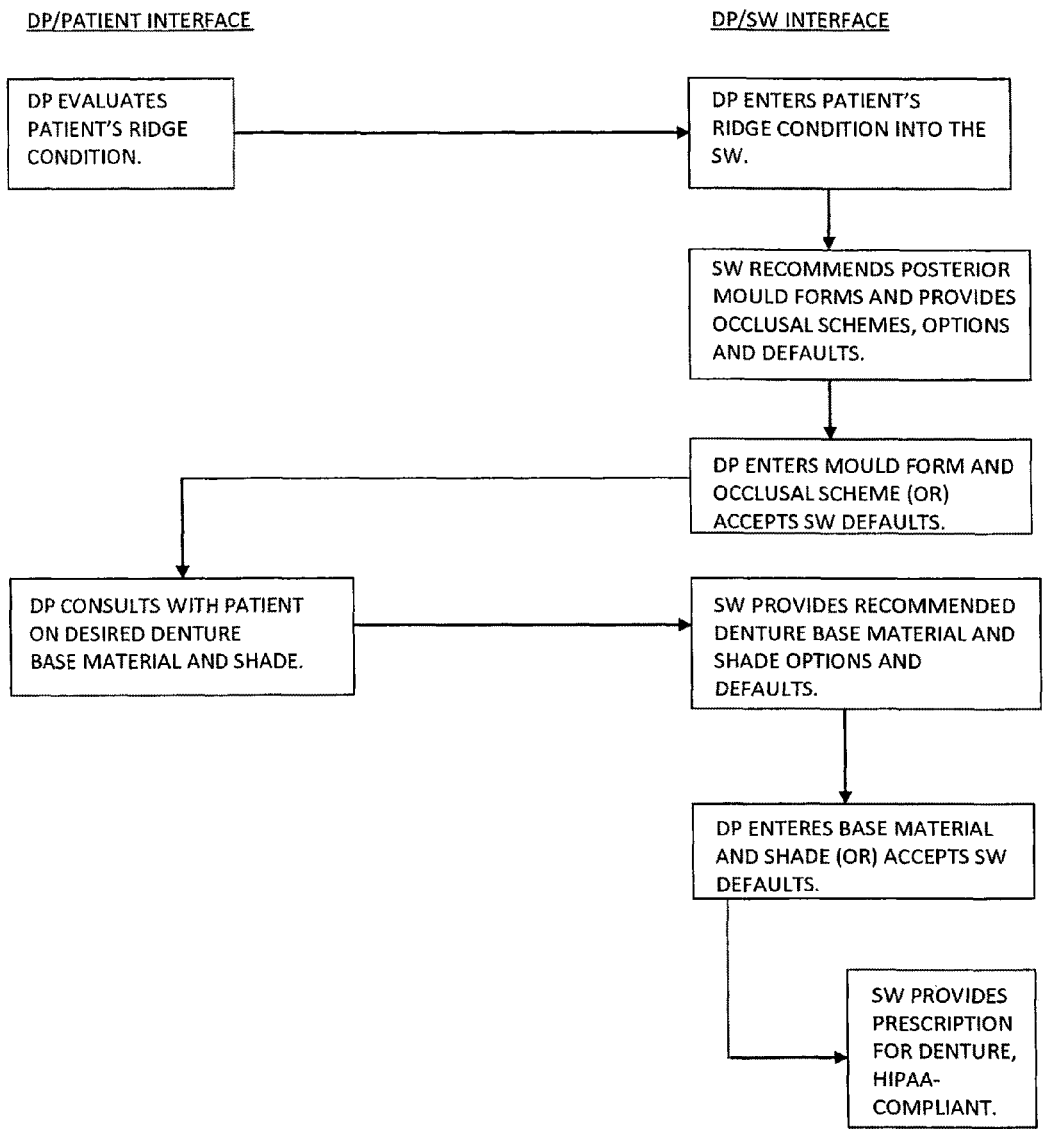

FIGURE 6
DENTAL SHADE GUIDES
○ TRUBYTE PORTRAIT IPN 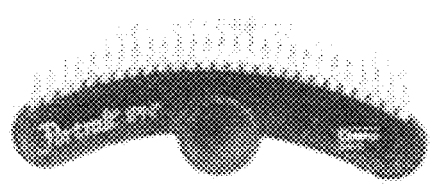
● TRUBYTE BIOBLEND IPN 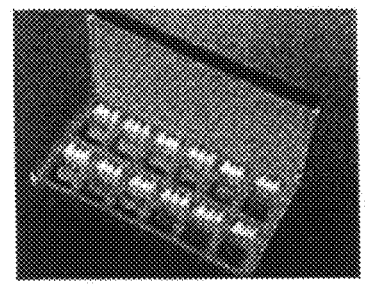
● TRUBYTE BIOFORM IPN 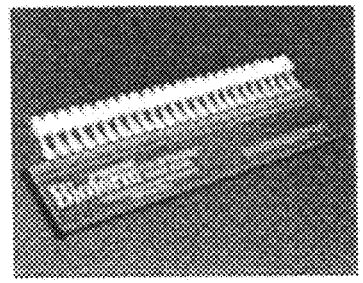

ANTERIOR MOULD FORMS

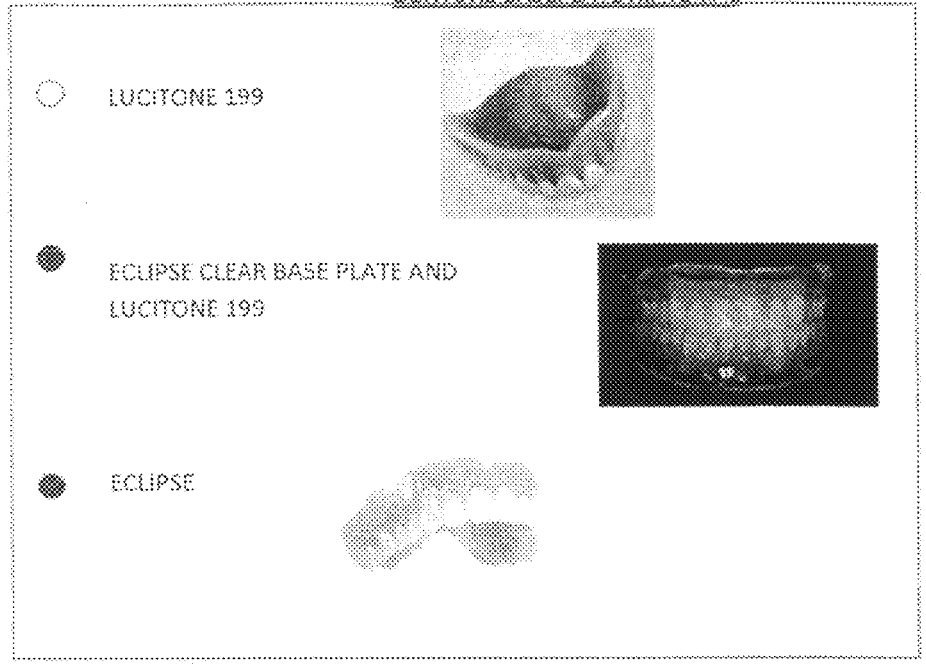
FIGURE 10
DENTURE BASEPLATE MATERIAL
○ LUCITONE 199
● ECLIPSE CLEAR BASE PLATE AND LUCITONE 199
● ECLIPSE
DENTURE BASEPLATE SHADE
BasePlate
○ ORIGINAL
● LIGHT PINK
● LIGHT REDDISH PINK
● DARK PINK
● CLEAR
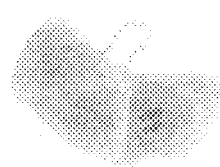

METHODS FOR DESIGNING A CUSTOMIZED DENTAL PROSTHESIS USING DIGITAL IMAGES OF A PATIENT

BACKGROUND OF THE INVENTION

1. Field of the Invention

The invention relates generally to methods for designing customized dental restorations and prostheses and particularly dentures. The methods involve taking digital photographs of the patient to be fitted with the restoration or prosthesis and transferring the photographs to a computer software program. The software program uses the photographs to make certain calculations that are translated into their corresponding anterior maxillary tooth mould forms. The program prompts the dental professional to select the desired materials and structure for the denture, such as denture tooth shade, tooth arrangement, patient ridge condition, occlusal scheme, and denture base. This information is used to generate a customized prescription for the denture. The resulting prescription is sent to a dental laboratory that manufactures the denture.

2. Brief Description of the Related Art

Dental professionals use different dental prostheses or appliances to treat patients with lost teeth or tooth structure. By the terms, "prosthesis," "restoration" "and "appliance" as used herein, it is meant a dental product that replaces or restores lost tooth structure, teeth, or oral tissue including, but not limited to, fillings, inlays, onlays, veneers, crowns, bridges, full dentures, removable partial dentures, relines of full and partial dentures, nightguards, occlusal splints, and the like. Common dental prostheses for full or partially edentulous patients include, for example, full dentures and partial dentures. The dentures are used to restore or replace the lost teeth. In general, removable partial dentures are used to replace some, but not all, of the patient's natural teeth. The partial denture includes a base having a partial set of embedded artificial teeth which rests in the edentulous space and is coupled to abutment teeth by clasps or other connectors. Full dentures, on the other hand, are used to replace all of the patient's natural teeth. A full denture includes a base having a full set of embedded artificial teeth which fits over either the upper gum tissue or lower gum tissue. Partial dentures are designed to preserve any remaining teeth along with hard and soft oral tissue. The dentures must be functional. Furthermore, the denture should enhance the dental and facial aesthetics of the patient. The denture teeth should appear natural. However, it is often difficult to make form-fitting and comfortable dentures. The process is time-consuming requiring the patient to make several dental office visits. In many instance, the dentist must reshape and adjust the denture several times before the patient is satisfied.

Today, a variety of methods are used to make dentures. In one traditional method, a dentist first takes impressions of a patient's dental anatomy. A paste-like material, such as an alginate, is placed in a standard or custom-made impression tray. The dentist inserts the tray in the mouth of a patient and he/she bites down into the tray. Separate impression trays for the upper and lower dental arches are used. The dentist allows the impression material to harden and then removes the trays from the patient's mouth. The hardened impressions are finally sent to a dental laboratory. There, a dental technician prepares models of the upper/lower dental arches by pouring dental stone into the hardened impressions. After a release coating is applied to the dental models, they are placed in a conditioning oven and warmed. A polymerizable resin used to form the baseplate is molded over the warm models. Then, the resin-coated models are placed in a light-curing unit and irradiated with light to harden the baseplate resin. After the light-curing cycle has been completed, the models are removed from the unit and allowed to cool. The hardened baseplates are removed from the respective models. It is customary for the technician to mount wax occlusal rims over the baseplates. The resulting wax rim baseplates are returned to the dentist so they can be evaluated for fit and comfort in the patient's mouth. Then, the completed occlusal registration is articulated.

Next, artificial teeth are built on the processed baseplate and wax rims using a "lost wax" process. In this method, wax is applied to the baseplate and a set of artificial teeth is positioned in the wax. The processed baseplate, with completed tooth arrangement, is placed in a flask containing an investing material. Then, the flask is heated to eliminate the wax. Upon melting, the wax flows out of the flask. Removing the wax from inside of the flask leaves an interior cavity having the shape of the denture. In a next step, a polymerizable acrylic composition is "packed into" into the interior cavity of the flask. The acrylic composition is heated so that it bonds to the teeth and baseplate. When this acrylic composition cures and hardens, it will hold the artificial teeth in position.

Designing and fabricating dentures is a complex process. Many time-consuming steps must be followed to prepare a denture having good aesthetics and mechanical properties. Artificial teeth having the proper color, shade, translucency, length, width, and geometry must be selected and incorporated into the baseplate. The process involves numerous dental professionals including dentists, dental assistants, and laboratory technicians and their work must be carefully coordinated to produce an aesthetically-pleasing and functional denture.

In recent years, computer-based systems using digital images have been developed so that certain dental prostheses can be made more efficiently in a time-saving manner. For example, Lehmann, U.S. Pat. No. 6,786,726 discloses a computer network system for making prostheses such as caps, crowns, bridges, fillings, and the like. In this method, the dental practitioner takes a digital image of the patient's tooth (resulting in a real image). A reference tooth shade (resulting in a reference image) image is also taken. The real and reference images are correlated to find a composite match number having an associated shade. The images are forwarded via computer network to a dental laboratory giving a dental technician access to the images. This allows both the dentist and technician to have simultaneous access to the images—they are able to evaluate the patient's case and develop a treatment plan together using the interactive network.

Jelonek, U.S. Pat. No. 7,035,702 discloses a method for making dental restorations involving the steps of determining the geometrical and aesthetic constraints of the restoration. These constraints are inputted into a computer to mathematically select a recipe for producing the dental restoration. A database of materials and procedures for preparing the dental restoration is compiled. Then, a recipe for making the restoration is produced from the database based on inputted data.

Taub, U.S. Pat. No. 7,33,874 discloses methods for designing and producing dental prostheses using a communication network between a dental clinic and dental laboratory. The system also includes a dental service center which is a separate entity from the dental laboratory. The service center generates a virtual 3D model of the patient's dentition from data obtained by scanning the teeth directly or by scanning a physical model of the teeth. The manufacturing of the prosthesis is shared between the service center and dental lab. The clinic sends instructions to the dental laboratory and service center. In one example, the data needed to produce the virtual 3D model is transmitted from the dental clinic or laboratory to the dental service center. A prescription specifying the teeth that are to be moved in the dental treatment as well as the final position of the teeth is sent to the service center. Then, the service center uses software to make a virtual 3D model, which is used to determine the dental appliance needed. Finally, this information is sent to the dental lab which makes the appliance.

The above-described systems may provide some advantages, but they are not used for designing and making dentures for edentulous patients, which present particular problems. As described above, in a conventional denture-making process, the dentist must manually measure the facial and oral dimensions of the patient, and selects artificial tooth colors, shades, and dimensions using manual tools such as tooth indicators, shade guides, and mould guides. Based on this information, the dentist sends a prescription for the denture to a dental laboratory. There are many variables to this process and the resulting prescription for the denture depends upon the techniques, skills, and experience level of the dental professionals. Some prescriptions will provide detailed information about the requested denture including patient's dental anatomy, baseplate materials, tooth dimensions and shapes, tooth color and shades, and the like. Other prescriptions will simply request the denture be made as the laboratory sees fit and will only provide information on the tooth shade.

The methods and system of the present invention provides the dental professional with a new chair-side method for writing denture prescriptions. The dentist can use the system to generate detailed digital prescriptions including information on facial dimensions of the patient, tooth length, width and geometry, requested composition of the artificial teeth, edentulous ridge condition and occlusal registration of the patient, denture base materials, and color and shade of the artificial teeth. The resulting prescription can be sent by e-mail, paper mail, or facsimile to a dental laboratory that will manufacture the denture. This system is easy-to-use, consistent, and time-saving for the dentist.

BRIEF DESCRIPTION OF THE DRAWINGS

The novel features that are characteristic of the present invention are set forth in the appended claims. However, the preferred embodiments of the invention, together with further objects and attendant advantages, are best understood by reference to the following detailed description in connection with the accompanying drawings in which:

FIG. 1 is a block functional diagram showing the general steps of preparing a denture in accordance with one embodiment of this invention;

FIG. 6 is a computer screen shot showing different dental shade guides that can be used in accordance with this invention;

FIG. 10 is a computer screen shot showing different denture base materials and baseplate colors for a patient to be fitted with a denture that can be used in accordance with this invention.

DETAILED DESCRIPTION OF THE INVENTION

The present invention provides different methods for designing customized dental restorations and prostheses, particularly dentures, using digital images. Although the methods described herein primarily refer to dentures, it should be understood that other dental restorations and prostheses can be designed in accordance with the invention. Referring to FIG. 1, the functional steps for designing and preparing a denture in accordance with one version of the invention are generally shown. Particularly, in Step 1, the dental practitioner takes at least one digital photograph of a patient's face and transfers the photograph to a computer software program.

Figure 2:
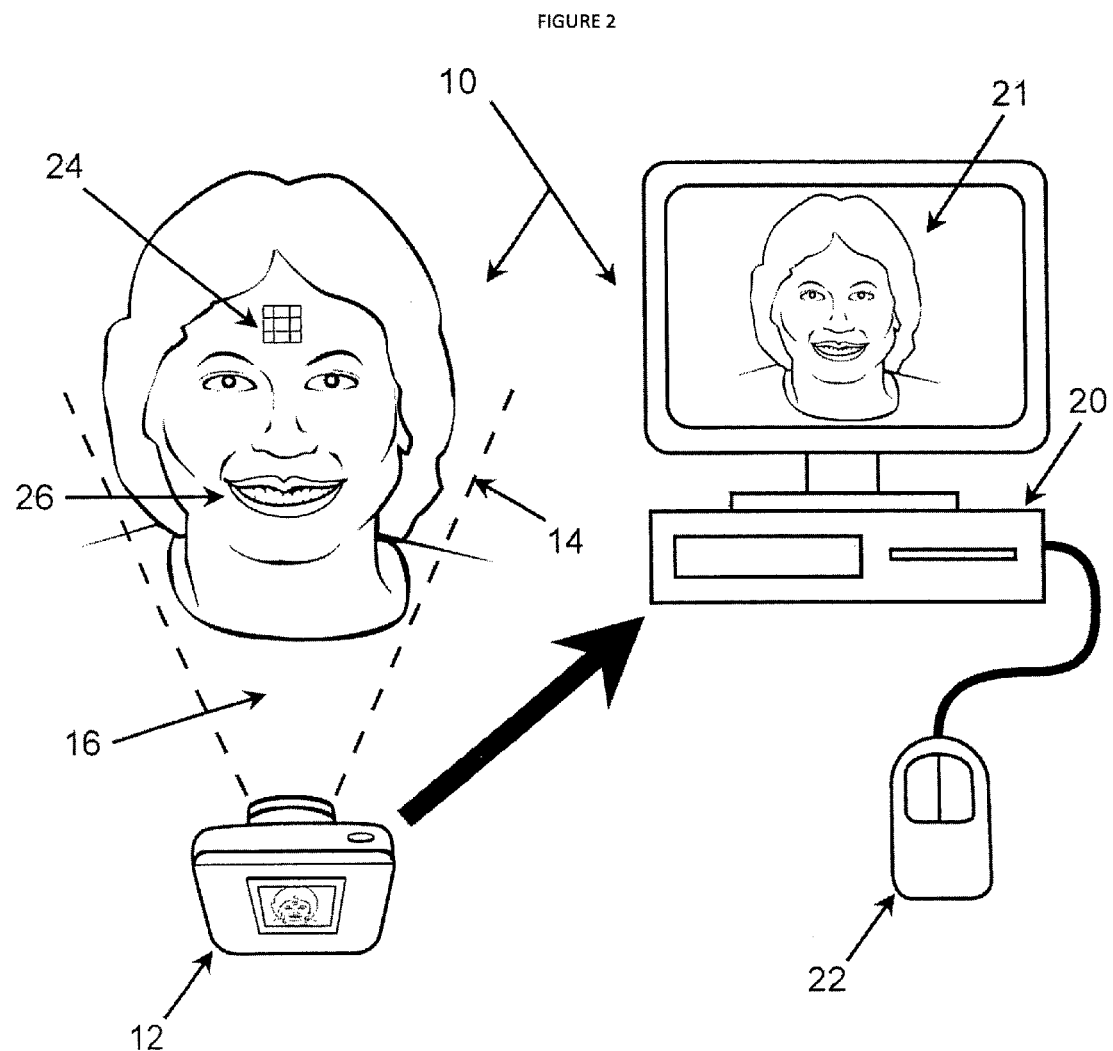
FIG. 2 is a schematic diagram showing a digital imaging system that can be used to prepare a denture in accordance with one embodiment of this invention.

Referring to FIG. 2, a digital imaging system, which can be used in the system and method, is generally indicated at (10). Ordinary digital cameras (12) can be used to take color digital photographs of a patient (14). Preferably, only one color digital photograph of the patient's face is taken, the photograph being a frontal view (16). Additional color digital photographs, however, can be taken if needed. For example, a profile or side view photograph of the patient could be taken. The digital photographs are loaded in a software program which is loaded in a computer (20) that includes a user interface system such as keyboard and/or mouse (22). The software can be packaged in any conventional way, for example, as a compact disc (CD). The software provides the user with interface tools such as graphic icons, images, text, windows, menus, and other screen displays so he/she can navigate their way through the program and complete the steps required to generate a denture prescription.

Figure 3:
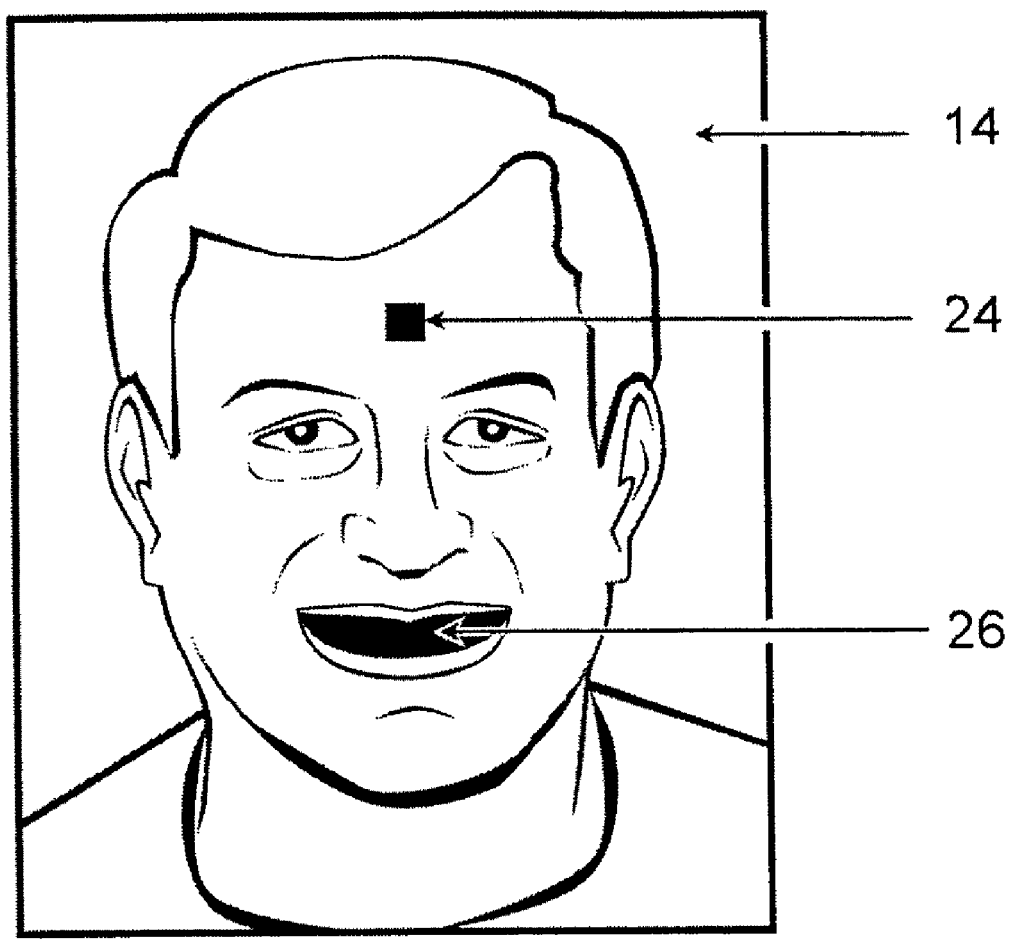
FIG. 3 is a perspective frontal view of a patient ready to be photographed with the digital imaging system of this invention.
Figure 4A:
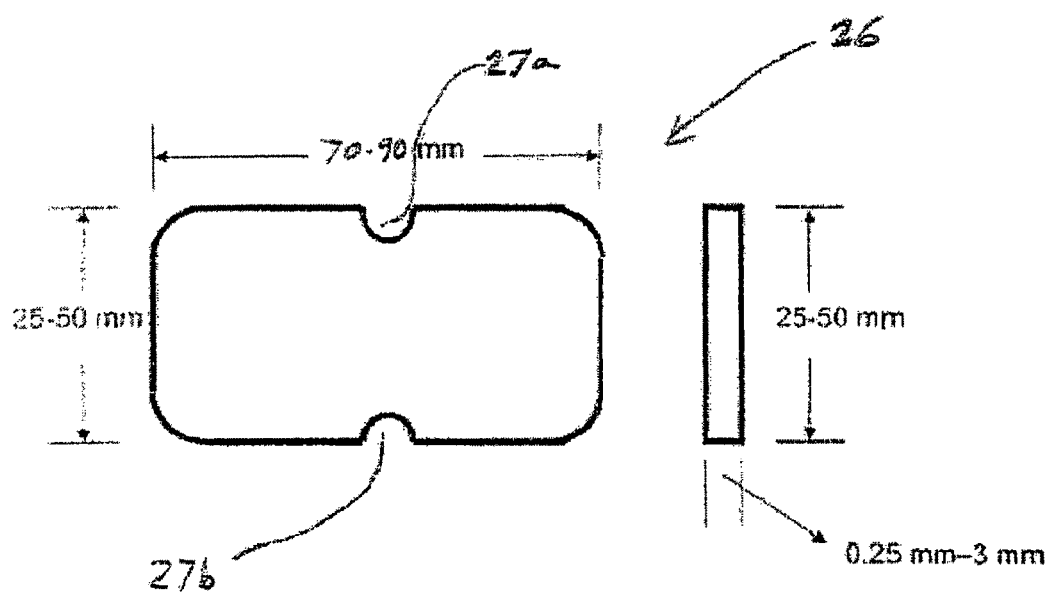
FIG. 4A is a perspective view of a mouth shield for placing in the mouth of a patient to be photographed with the digital imaging system of this invention.
Figure 4B:
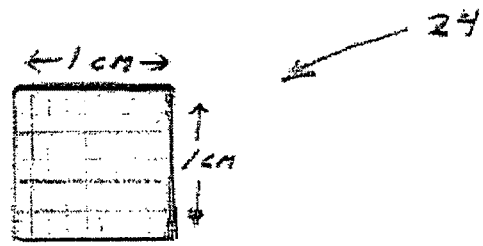
FIG. 4B is a perspective view of a reference sticker for placing on the forehead of a patient to be photographed with the digital imaging system of this invention.

Prior to taking the digital photographs, a grey screen reference sticker" (24) is placed on the forehead of the patient and a grey screen mouth shield" (26) is positioned inside the mouth of the patient. The sticker (24) and mouth shield (26) are used so that a grey screening and color balancing procedure can be performed as described further below. In FIG. 3, a frontal view of a patient (14) wearing reference sticker (24) and mouth shield (26) is shown. Referring to FIG. 4A, the mouth shield (26) has a ribbon-like structure with notched portions (27a, 27b). The mouth shield (26) is made from a thin, soft, and flexible material. The mouth shield should have good dimensional stability and be sufficiently rigid so that it retains its position once it is placed inside of the mouth Suitable materials for making the mouth shield (26) include, but are not limited, to urethane foam and flexible wax-based sheets. The mouth shield (26) is designed to fit most patients and has a length in the range of about 70 to about 90 mm;

width of about 25 to about 50 mm; and thickness of about 0.25 to about 3 mm. The mouth shield (26) is placed in the mouth of the patient (14) and folded over at notched portions (27a, 27b) so that it is tightly secured between the gums and lips. To adjust the fit of the mouth shield (26) for a given patient, scissors can be used to trim excess portions. As shown in FIG. 3, the mouth shield (26) resembles an athletic mouth guard when positioned in the mouth of the patient (14). As shown in FIG. 4B, the removable reference sticker (24) is a paper or film material having an adhesive coated on its backside. The square-shaped sticker (24) generally measures about 1 cm×about 1 cm. The sticker (24) can be placed on the forehead of the patient and removed after the photographs have been taken.

The color grey preferably is used for the reference sticker (24) and mouth shield (26), because it contrasts sharply with other skin colors and the patient would not normally be wearing any other grey object on his/her face when taking the photographs. In "grey screening," the system checks to see which pixels in the input image (digital color photograph) are not grey and labels those pixels as "target" pixels. The software then blends the "input image" (patient's facial image, which is a collection of all target pixels) into a "destination image" that will appear on the computer monitor screen (21). The pixels in the grey areas are not labeled as target pixels and thus will not be blended in with the rest of the pixels constituting the facial features.

This technique of blending two images together after a color has been removed from one of the images can be referred to as chroma keying. This results in the input image (facial image) having "color voids" or "color removal points" (where pixels are missing) upon being blended into the destination image. Particularly, voids will appear in the area of the forehead (where the grey screen sticker has been placed) and area of the mouth (where the grey screen mouth shield has been inserted).

The software program first looks to the forehead area. Because the software knows the relative dimensions of the grey sticker (24), it can use this information to make key measurements of the forehead and other facial contours. In addition, the software fills in the voided mouth area with selected tooth shades and tooth forms per the methods discussed further below. That is, the practitioner can select a particular denture structure with artificial teeth and "drop" this picture into the open mouth area of the digital image. The resulting destination image with selected denture is shown to the patient. Thus, the patient can see the results of selecting a specific denture before the treatment plan is finalized. The patient can see how a particular denture structure will affect their overall appearance. The system is beneficial to the practitioner and patient, because it can simulate different treatment plans using different sets of artificial teeth.

Upon receiving the digital image, the software automatically engages in color balancing to adjust the color of the captured digital image and generate a color balanced reproduction. Color balancing techniques are known in the digital imaging industry. Color balancing is needed, because colors in the captured digital image can shift resulting in an off-color image of the subject. Color shifting can be due to a variety of reasons, for example, shadows, lighting, and backdrops used when the digital image was taken. In the method of this invention, the colors of the facial image of the patient can become distorted; thus, color balancing of the image is needed. Once the digital image has been properly color balanced, a selected artificial tooth set can be "dropped' into the image and a denture prescription can be generated as described in more detail below. In the color balanced digital image, the color of the selected "dropped in" tooth set is perceived correctly. That is, the color, shade, hue, brilliance, intensity, RGB values, and other characteristics of the tooth set and facial digital image match-up properly. This benefits the dental practitioner, because he/she is better able to select the most appropriate tooth shade with input from the patient. The practitioner and patient can better visualize which tooth shade is the most natural looking.

It is recognized that other imaging techniques can be used in accordance with this invention. For example, a "green-screening" system can be used, wherein the reference sticker (24) and mouth shield (26) are green colored. However, a "green-screening" system is less preferred, because there can be problems with color balancing and the captured digital image may be off-color.

Figure 5:
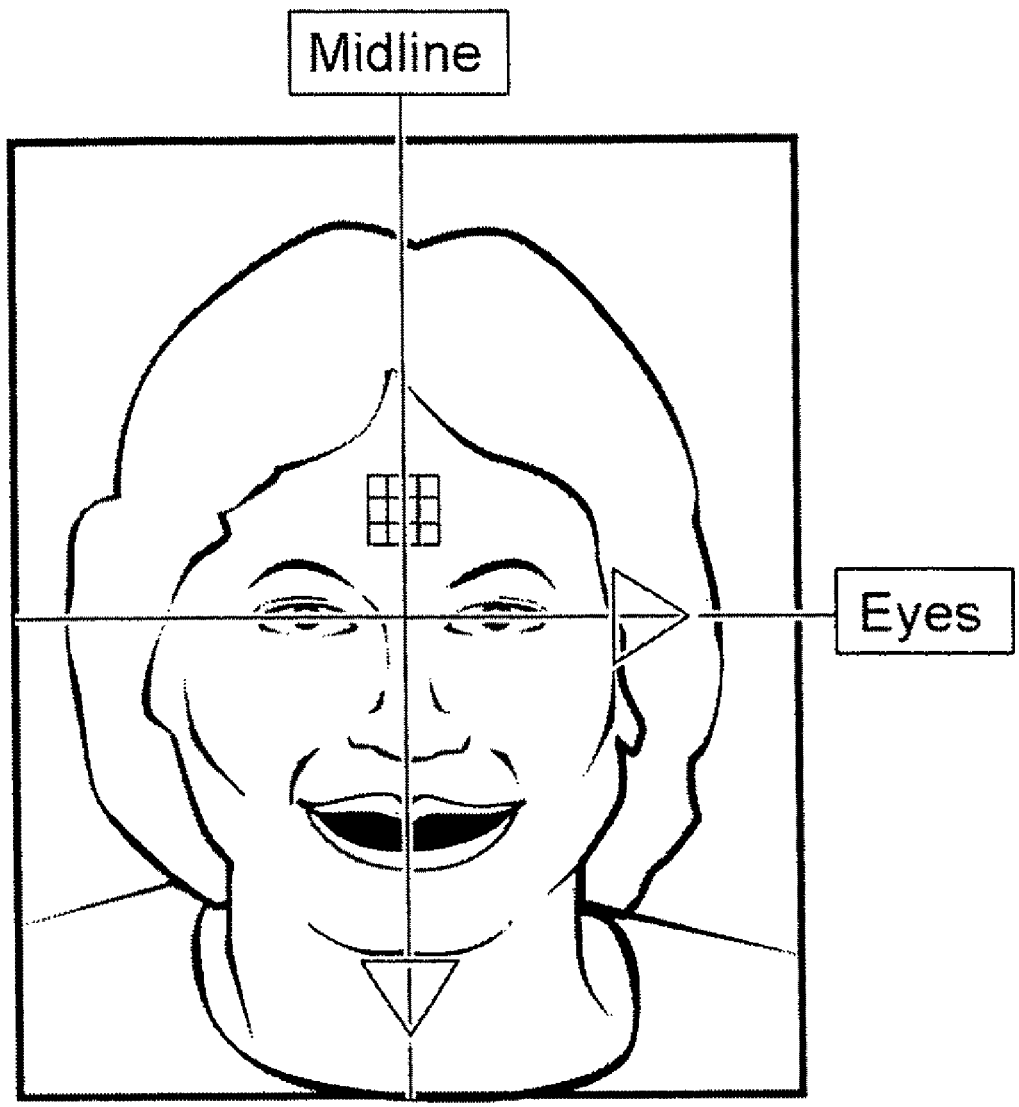
FIG. 5 is a perspective view of a digital image of a patient showing facial contours marked with reference lines.

In addition to the color balancing step, the software automatically formats the digital image to the correct size, and the formatted, color-balanced image appears on the monitor screen (21) so that the practitioner can view it easily. The software program then identifies the key facial contours, for example, chin, temple, vertical midline, and horizontal plane across the pupils. It is important that vertical and horizontal reference planes of the patient's face be considered so that an aesthetically-pleasing denture with artificial teeth having proper occlusion can be made. The program identifies the vertical midline and horizontal plane across the pupils as shown in FIG. 5. The dental practitioner can use the reference lines automatically provided by the program if they are acceptable. Alternatively, the practitioner can override the recommendations made by the program and mark key facial landmarks that they believe are more accurate. The program then provides a recommended face shape that the practitioner again has the ability to accept or override with his/her own selection. In some instances, the program can include a "default" face shape. For example, the face shape, "square tapering" could be used as the default and this shape would be automatically entered if the user did not enter otherwise. Once the facial contours and face shape have been entered and accepted by the practitioner, the software automatically determines the width and length of the central incisor artificial teeth that will be used in the denture. The practitioner also has the ability to accept or decline these measurements and enter his/her own measurements. After all of the requested information has been entered and accepted, the program will provide the recommended maxillary anterior denture tooth mould forms to be used for making the artificial teeth as discussed further below.

Referring back to the block diagram in FIG. 1, the dental practitioner next enters the color shade guide that will be used for determining the color and shade of the artificial teeth to be used in the finished denture. Standard dental shade guides are known in the dental industry and these guides can be used in the system of this invention. For example, Portrait™ IPN™, Trubyte Bioform™ IPN™, or Bioblend™ IPN™, shade guides available from Dentsply International (York, Pa.) can be used. Other suitable shade guides include Vita Classical™ and Vita 3-D™ shade guides available from Vita Zahnfabrik H. Rauter GmbH & Co. KG (Germany). The software can provide the practitioner with at least two, and more preferably three shade guide options, to select there from. For example, the software can be programmed so that the text and/or graphic icons of the shade guides: Portrait IPN, Bioform IPN, and Bioblend IPN appear on the computer monitor screen. For example, referring to FIG. 6, a screen shot shows three possible shade guide select options. The user can enter the desired shade guide by "clicking" on the mouse and selecting a shade guide from this predetermined set. In some instances, the program can further include a default shade guide. So, if the user does nothing, the default shade guide is automatically selected. In FIG. 6, the first shade guide option (Portrait IPN) is designated as the default selection for illustration purposes.

In accordance with this invention, the dental practitioner uses a tangible, hand-held shade guide (not shown) to select the most appropriate tooth color and shade. As noted above, shade guides are well known in the dental industry. The shade guides include removable colored tabs. The colored tabs come in a variety of shades resembling the appearance of natural teeth. Each shade provides a unique enamel translucency, color blending, and contrasting colors between neck and body of the artificial tooth. To determine the appropriate tooth shade for a given patient, the practitioner removes one of the tabs and holds it up in the mouth of the patient. Together, the practitioner and patient decide upon the appropriate tooth shade. In making this decision, the practitioner and patient address such questions as: Which tooth shade is the most natural looking? Which tooth shade will complement the patient's natural features? And, which tooth shade will enhance cosmetic appearance? The selected tooth shade from the given tooth shade guide is then entered. The software program may provide a drop-down menu on the monitor screen (21) listing each of the predetermined tooth shades for a given shade guide. The practitioner can enter the desired shade by simply scrolling down the menu and clicking on the shade guide in this predetermined set. For example, the Portrait IPN dental shade guide includes 27 translucent shades ranging from shades designated as "P1 to P81." If the practitioner and patient decide that "P2" tooth shade is the best match, the practitioner can enter this shade into the program. In turn, the program can generate an image simulating a denture with the selected tooth shade. Thus, the patient can see the effect of selecting a specific tooth shade and how this shade will impact their appearance. The program also can provide side-by-side comparisons of a denture made with a first tooth shade against a denture made with a second and different tooth shade. These images should be used for comparison references only. In considering which tooth shade would provide the best aesthetics for a given patient, the practitioner should use an actual hand-held tooth shade guide as described above.

Next, the program recommends a denture tooth mould form that will be used for making the denture. The mould form is chosen based on facial contours, tooth measurements, patients ridge condition, and tooth shades entered according to the steps described above. Moulds for making teeth are well known and include the Bioform® mould system; and Biostabil®, Monoline®, Anatoline®, and Euroline® posterior mould forms, available from Dentsply. As indicated, the moulds are available in anterior and posterior forms. The anterior moulds are used for producing the anterior teeth (central incisors, lateral incisors, and canines), while the posterior moulds are used for producing the posterior teeth (premolars and molars). For example, if the Portrait IPN tooth shade guide (as discussed above) is used, there are 62 anterior mould and 27 posterior occlusal mould forms available based on the Bioform mould system (tapered at angles of 0, 10, 20, 22, 33, and 40 degrees) that can be used. On the other hand, if the Bioblend IPN tooth shade guide (as discussed above) is used, there are 58 upper and lower anterior mould form options and 4 posterior occlusal mould forms available. The appropriate artificial tooth mould form for making the denture can be recommended from these sets and displayed on the computer screen allowing the practitioner to select there from.

Figure 7:
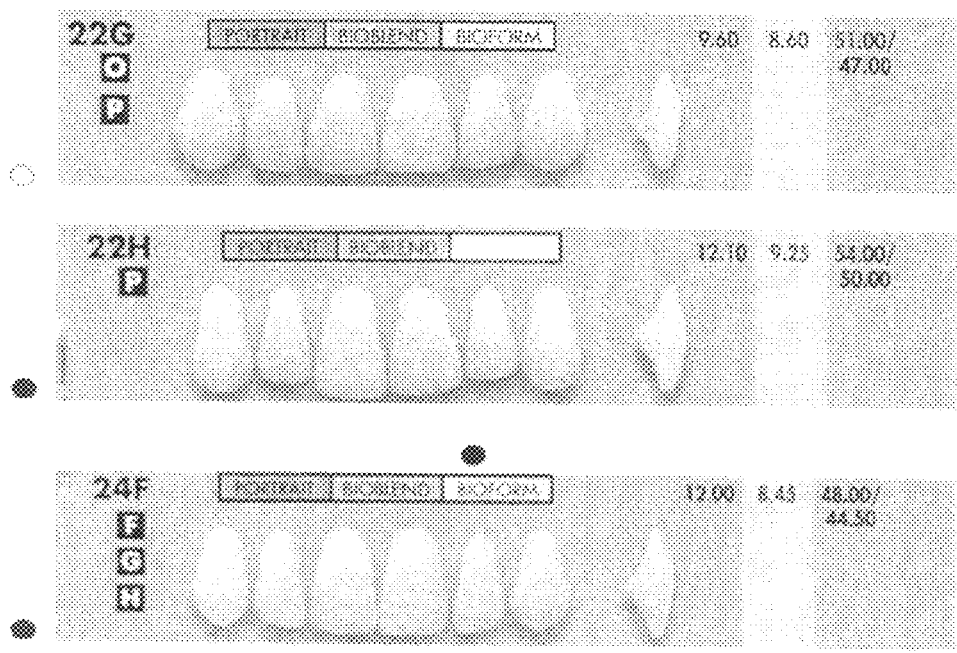
FIG. 7 is a computer screen shot showing different tooth mould forms that can be used in accordance with this invention.

In one preferred embodiment, in the anterior region, at least two, and more preferably, three tooth mould form options are provided by the software program. The user can enter the desired anterior mould form based on these predetermined select options. Referring to FIG. 7, a screen shot of the monitor shows three possible anterior mould form options. The user can simply click on the mouse, thereby selecting an anterior mould form from this predetermined set. In some instances, the program can further include a default anterior mould form. For example, in FIG. 7, the first mould form is designated as the default selection. Alternatively, if the practitioner wishes, he/she can decide to over-ride the given options and enter a different tooth mould form. In addition, the practitioner, in consultation with the patient, enters the appropriate anterior tooth arrangement that will provide the desired aesthetics and function in the finished denture. In one preferred embodiment, the program can provide three anterior tooth arrangements as options, and the practitioner can select any one of these arrangements.

Figure 8:
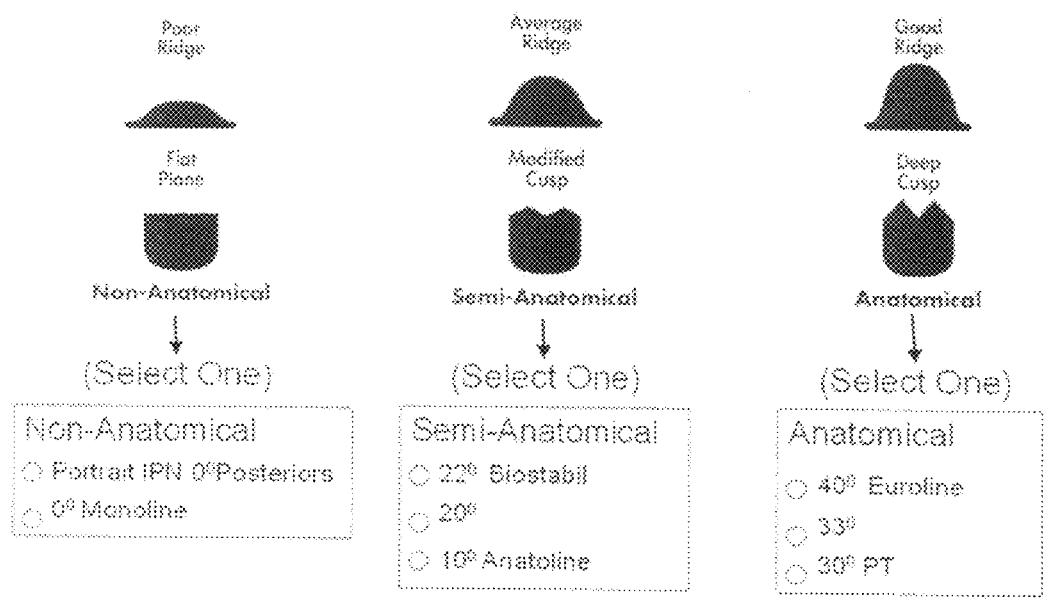
FIG. 8 is a computer screen shot showing different edentulous ridge conditions of a patient to be fitted with a denture that can be used in accordance with this invention.

Following the functional steps illustrated in FIG. 1, the practitioner next evaluates the edentulous ridge condition of the patient and enters this information. The edentulous ridge refers to the remaining portion of the alveolar ridge and soft tissue after the teeth have been removed. The practitioner evaluates and generally characterizes the ridge condition as being either poor, average, or good. The program can provide these three options for selection as shown in the computer screen shot of FIG. 8. The practitioner enters the ridge condition that most closely resembles the patient's actual condition. Based on the edentulous ridge condition, suitable posterior denture tooth mould form options are provided as shown in FIG. 8. The practitioner can select the desired mould form from the set displayed on the computer screen. For example, if the patient has an average ridge condition, then the posterior mould form options: Biostabil® (tapered at 22°); (tapered at 20°) and Anatoline® (tapered at 10°), are displayed, and the practitioner selects one of these mould forms.

Figure 9:
FIG. 9 is a computer screen shot showing different occlusal schemes for a patient to be fitted with a denture that can be used in accordance with this invention.

In addition, the practitioner enters the desired occlusal scheme for the patient. Several occlusal scheme select options can be provided by the software as shown in the computer screen shot of FIG. 9. For example, the occlusal schemes can be classified as: a) bilateral balanced, b) lingualized, or c) linear, and the practitioner can select from one of these options. In FIG. 9, the bilateral balanced option is designated as the default occlusal scheme for illustration purposes. If the practitioner wishes, he/she can accept this default option.

The material that will be used to make the denture is also entered. The practitioner can work with the patient in making this decision or accept the default selections made by the program. A set of predetermined denture base materials preferably is loaded in the software program and appear as select options on the computer screen as shown in FIG. 10. For example, denture bases made from such materials as Lucitone 199® acrylic resin or Eclipse® baseplate resin which is a wax-like polymerizable material, both available from Dentsply can be added as predetermined selections. In this example, the user can enter the desired denture base material by clicking on the mouse and selecting either Lucitone 199® acrylic resin or Eclipse® baseplate resin. The desired color of the baseplate also needs to be entered. The baseplate color can be entered by selecting a color from a wide variety of select color options provided by the program. As also shown in FIG. 10, several color options intended to resemble healthy gum tissue can be provided including light pink; light reddish pink; and dark pink. Alternatively, the baseplate can be clear and transparent. Eclipse® baseplates are available in a clear version. Desired denture base materials and colors can be selected from the automatically programmed sets. In preferred cases, the program includes default select denture base materials and colors. For example, in FIG. 10, Lucitone 199® acrylic resin in its original color is designated as the default selection.

It should be understood that the functional steps shown in the block diagram of FIG. 1 are for illustrative purposes only and are not meant to be restrictive. In other versions, it is contemplated that some of the steps could be eliminated to expedite the method for generating the customized prescription. Also, it is anticipated that the sequence of steps could be changed in some instances depending upon the needs of the practitioner and patient. As shown in FIG. 1, the output of the system, based on the input of data and other information as described above, is a digital prescription for making a denture for the given patient. The customized digital prescription includes detailed information on facial dimensions of the patient, tooth length, width and geometry, requested composition of the artificial teeth, edentulous ridge condition and occlusal scheme, denture base materials, and color and shade of the artificial teeth. In addition, the digital prescription is HIPAA-compliant. One example of such a digital prescription is shown below.

EXAMPLE OF DIGITAL PRESCRIPTION

Facial Classification: Square tapering
Tooth Length: 9.60
Width of the anterior teeth: 8.60
Denture tooth composition: Premium IPN
Ridge condition: Average
Occlusal scheme: Bilateral balanced
Denture base material: Lucitone 199® acrylic resin
Denture base color: Original
Shade guide: Portrait™
Anterior shade: P2
Posterior shade: P2
Maxillary

| Anterior Teeth: | Posterior Teeth: |
|---|---|
| Shade P2, Mould 22G | Shade P2, Mould 31M |

Mandibular

| Anterior Teeth: | Posterior Teeth: |
|---|---|
| Shade P2, Mould P | Shade P2, Mould 31M |

Figure 11:
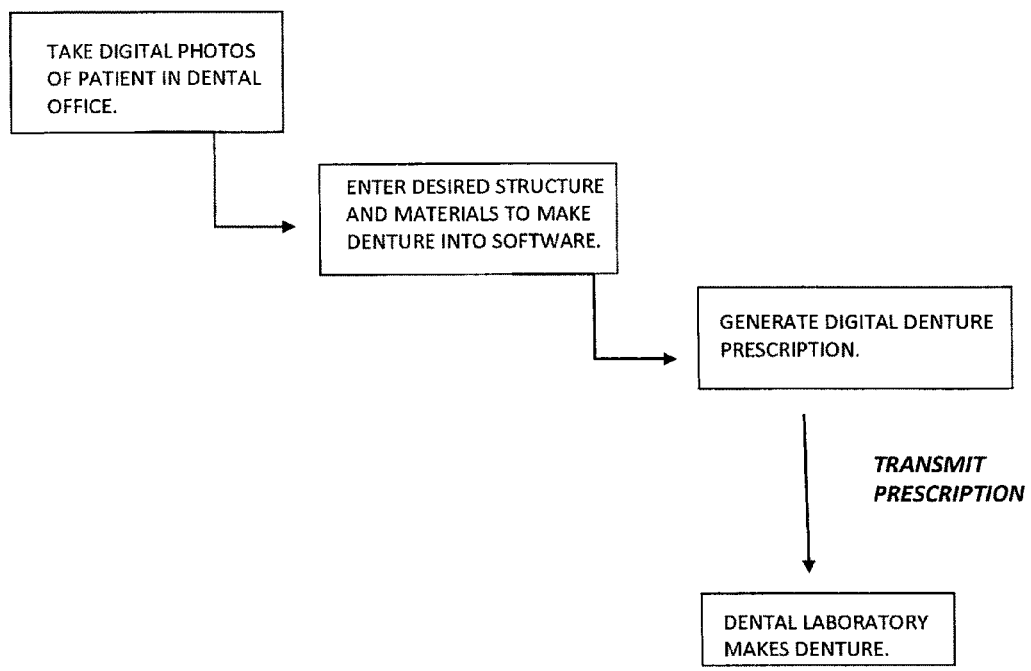
FIG. 11 is a schematic diagram showing the general steps of designing and making a denture in accordance with one embodiment of this invention.

The resulting customized digital prescription can be sent by e-mail, facsimile, paper mail, or other means to a dental laboratory that will manufacture the denture. In addition, a copy of the digital prescription can be provided to the patient for his/her records. The dental laboratory can use conventional techniques to fabricate the denture as prescribed. In FIG. 11, a schematic diagram showing the basic steps of generating a customized digital prescription and transmitting the prescription to a dental laboratory in accordance with this invention are shown.

The methods and systems of this invention provide the dental practitioner with a new tool for designing and making dentures. As described above, the dentist can use the system to generate customized digital prescriptions. In addition, the system can be used as a tutorial for patients and staff in the dental office. For practitioners, the system offers many benefits including a quick and accurate means for prescribing dentures and recording the prescriptions. The system helps the practitioner by providing a step-by-step guide to designing a customized denture for a given patient. The practitioner is led step-by-step through the procedure.

Particularly, the system provides reference points across the facial digital image(s) of the patient so that the dentist can more accurately identify facial contours. Based on this information, the system automatically provides facial and tooth measurements and provides suggestions for tooth shade and denture base shade. Furthermore, the system prompts the practitioner by asking key questions such as: What is the edentulous ridge condition of patient? What is the occlusal scheme? What is the desired tooth arrangement? This helps the practitioner design a close fitting and comfortable denture. The resulting denture helps enhance the appearance of the patient and is fully functional. The system also helps facilitate two-way communication between the practitioner and patient. Rather than the practitioner deciding on the make and style of the denture and dictating this to the patient one-way, the patient is invited to participate in the process. The patient is asked for input on the desired tooth shade and denture base shade along with other decision points. Thus, the system is more interactive—the practitioner and patient are more engaged in the process. Each person feels that he/she has more input and control over the design and fabrication of the denture.

Persons skilled in the art will appreciate that various modifications can be made to the illustrated embodiments and description herein without departing from the spirit and scope of the present invention. It is intended that all such modifications within the spirit and scope of the present invention be covered by the appended claims.

What is claimed is:
1. A method for producing customized denture prescriptions, comprising the steps of:
   a) placing a reference indicia on the face of a patient, the reference indicia having a predetermined dimension;
   b) positioning a mouth shield generally in the patient's mouth prior to the taking at least one digital photograph step, the mouth shield being dimensioned to cover at least a portion of the patient's teeth thereby creating a voided area in the digital photograph;
   c) taking at least one digital photograph of the patient's face;
   d) loading the photograph to a computer software program, wherein the program compares the predetermined dimension of the reference indicia to one or more other areas of the patient's face to identify and measure facial contours of the patient;
   e) creating an digital image of the digital photograph, the digital image being formatted relative to the identified and measured facial contours of the patient and the voided area;
   f) entering or selecting at least one of desired materials and structure for making the denture, in consultation with the patient, using the software program so that the program automatically produces a prescription for the denture based on the entered materials and/or structure;
   g) superimposing the entered or selected at least one of desired materials and structure for making the denture into the voided area of the digital image so that a practitioner or the patient can see the results of what the patient may look like with the selected combination; and h) transmitting the prescription to a dental laboratory for making the denture.

2. The method of claim 1, wherein one photograph of the patient's face is taken, the photograph being a frontal view.

3. The method of claim 1, wherein the tooth shade guide includes removable shade tabs.

4. The method of claim 1, wherein the facial contours of the patient are used to determine the length, width, and shape of artificial teeth used in the denture.

5. The method of claim 1, wherein entering the desired materials of the denture includes:
   a) entering tooth mould forms for the artificial teeth used in the denture;
   b) entering an edentulous ridge structure; or
   c) entering an occlusal scheme of the patient.

6. The method of claim 5, wherein anterior tooth mould forms are entered, posterior tooth mould forms are entered, or a combination of both.

7. The method of claim 1, wherein entering the desired materials for making the denture includes entering a denture baseplate material.

8. The method of claim 7, wherein the denture baseplate material has a color and shade matching the color and shade of the gum tissue of the patient.

9. The method of claim 7, wherein the denture baseplate material is substantially transparent.

10. The method of claim 7, wherein the denture baseplate material is made from an acrylic polymer or a wax-like polymerizable material.

11. The method of claim 1, wherein the prescription is transmitted to the dental laboratory via e-mail, paper mail, or facsimile and optionally is also provided to the patient.

12. A method for producing customized denture prescriptions, comprising the steps of:
   a) placing a reference indicia on the face of a patient, the reference indicia having a predetermined dimension;
   b) positioning a mouth shield generally in the patient's mouth prior to the taking at least one digital photograph step, the mouth shield being dimensioned to cover at least a portion of the patient's teeth thereby creating a voided area in the digital photograph;
   c) taking at least one digital photograph of the patient's face;
   d) loading the photograph to a computer software program, wherein the program compares the predetermined dimension of the reference indicia to one or more other areas of the patient's face to identify and measure facial contours of the patient;
   e) creating an digital image of the digital photograph, the digital image being formatted relative to the identified and measured facial contours of the patient and the voided area;
   f) entering or selecting at least one combination of materials and structure for making the denture, in consultation with the patient, including a desired tooth shade guide and tooth shade, the tooth shade being chosen from the selected tooth shade guide, from a set of predetermined materials and structures provided by the software program;
   g) superimposing at least one of the at least one combination of materials and structure for making the denture into the voided area of the digital image so that a practitioner or the patient can see the results of what the patient may look like with the selected combination;
   h) entering or selecting a desired combination of the at least one combination of materials and structure for making the denture so that the program automatically produces a prescription for the denture based on the selected materials and structure; and
   i) transmitting the prescription to a dental laboratory for making the denture.

13. The method of claim 12, wherein the set of predetermined structures and materials includes at least two options for selecting the dental shade guide.

14. The method of claim 13, wherein one shade guide option is set as a default option.

15. The method of claim 12, wherein the set of predetermined structures and materials includes:
   a) at least two options for selecting a tooth mould form for artificial teeth used in the denture;
   b) at least two options for selecting an edentulous ridge structure of the patient;
   c) at least two options for selecting an occlusal scheme of the patient; or
   d) at least two options for selecting a denture base material and at least two options for selecting denture base color.

16. The method of claim 15, wherein the tooth mould form options are for anterior teeth, posterior teeth, or a combination of both.

17. The method of claim 15, wherein a default option is set as:
   a) one mould form option;
   b) one occlusal scheme option; or
   c) one denture base material option is set as a default option and one denture base color.

18. The method of claim 12, wherein the prescription is transmitted to the dental laboratory via e-mail, paper mail, or facsimile and optionally is also provided to the patient.

* * * * *